United States Patent [19]

Butler et al.

[11] Patent Number: 4,723,050

[45] Date of Patent: Feb. 2, 1988

[54] XYLENE ISOMERIZATION PROCESS

[75] Inventors: James R. Butler; Kevin P. Menard, both of Big Spring, Tex.

[73] Assignee: Cosden Technology, Inc., Dallas, Tex.

[21] Appl. No.: 903,389

[22] Filed: Sep. 3, 1986

[51] Int. Cl.$^4$ .............................................. C07C 5/22
[52] U.S. Cl. ................................... 585/480; 585/477; 585/481
[58] Field of Search ....................... 585/477, 480, 481

[56] References Cited

U.S. PATENT DOCUMENTS

| | | |
|---|---|---|
| Re. 29,948 | 3/1979 | Dwyer et al. . |
| 3,856,872 | 12/1974 | Morrison . |
| 4,061,724 | 12/1977 | Grose et al. . |
| 4,159,282 | 6/1979 | Olson et al. . |
| 4,163,028 | 7/1979 | Tabak et al. . |
| 4,188,282 | 2/1980 | Tabak et al. . |
| 4,218,573 | 8/1980 | Tabak et al. . |
| 4,387,260 | 6/1983 | Watson et al. . |
| 4,400,571 | 8/1983 | Robinson ............................ 585/480 |
| 4,416,765 | 11/1983 | Chester et al. ................. 208/52 CT |
| 4,587,371 | 5/1986 | Forward et al. . |

FOREIGN PATENT DOCUMENTS 0000812 2/1979 European Pat. Off. ............ 585/481

OTHER PUBLICATIONS

Debras et al, "Physico—Chemical Characterization of Pentasil Type Materials I. Precursors and Calcined Zeolites," and II. Thermal Analysis of the Precursors, *Zeolites*, Nov. 1985, vol. 5, pp. 369-383.

*Primary Examiner*—Curtis R. Davis
*Attorney, Agent, or Firm*—William D. Jackson; John K. Abokhair; M. Norwood Cheairs

[57] ABSTRACT

Process for the isomerization of a xylene feedstock employing a silicalite catalyst. A xylene feedstock containing a mixture of xylene isomers and ethylbenzene is passed to a reaction zone containing the silicalite catalyst. Para-xylene is present in the feedstock in less than an equilibrium amount, and ethylbenzene is present in a concentration greater than the para-xylene concentration. Hydrogen and/or water are also supplied to the reaction zone. The reaction zone is operated under conditions to effect isomerization of xylene isomers to provide an increased para-xylene content, and disproportionation of ethylbenzene to provide a decreased ethylbenzene content.

16 Claims, 2 Drawing Figures

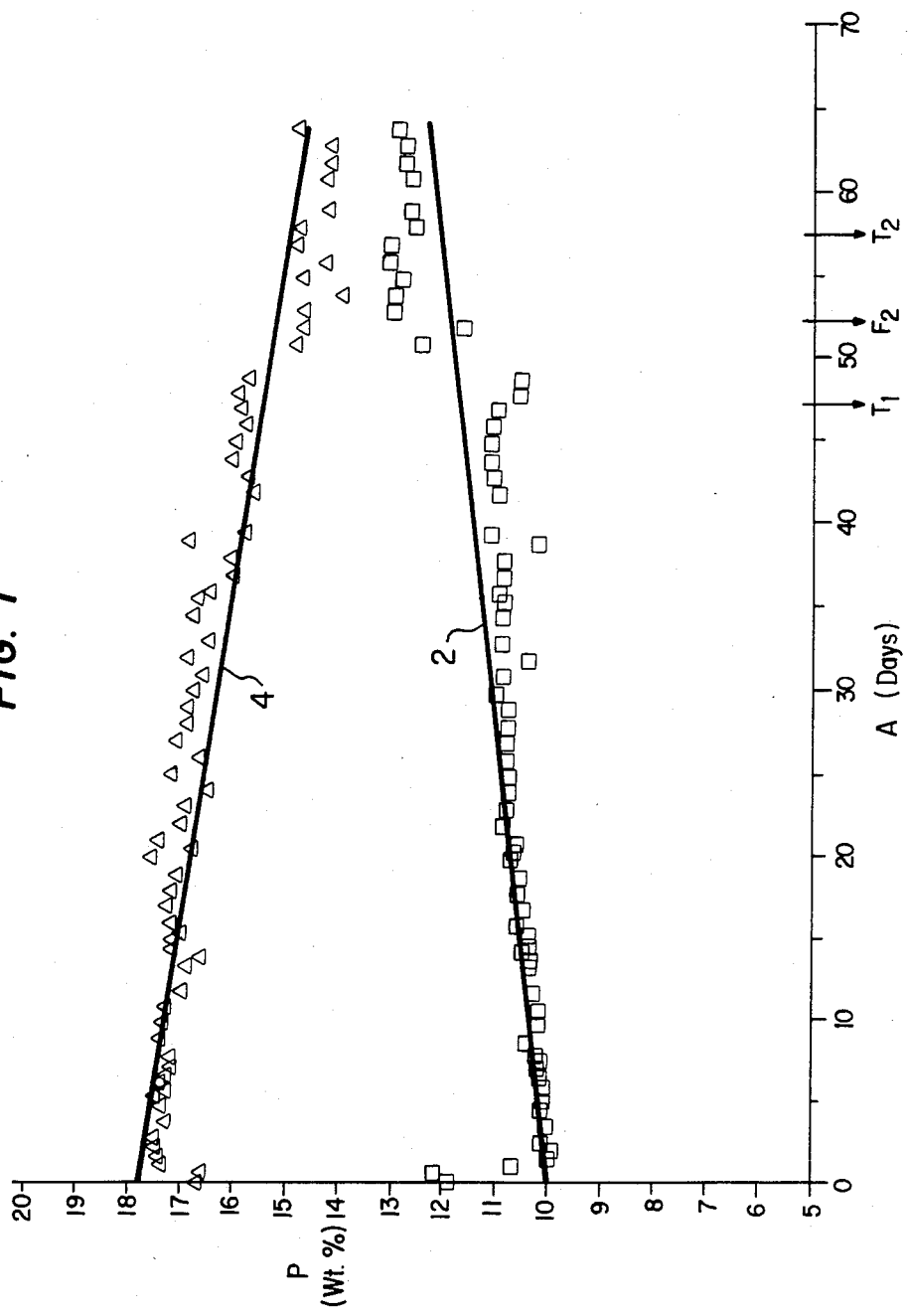

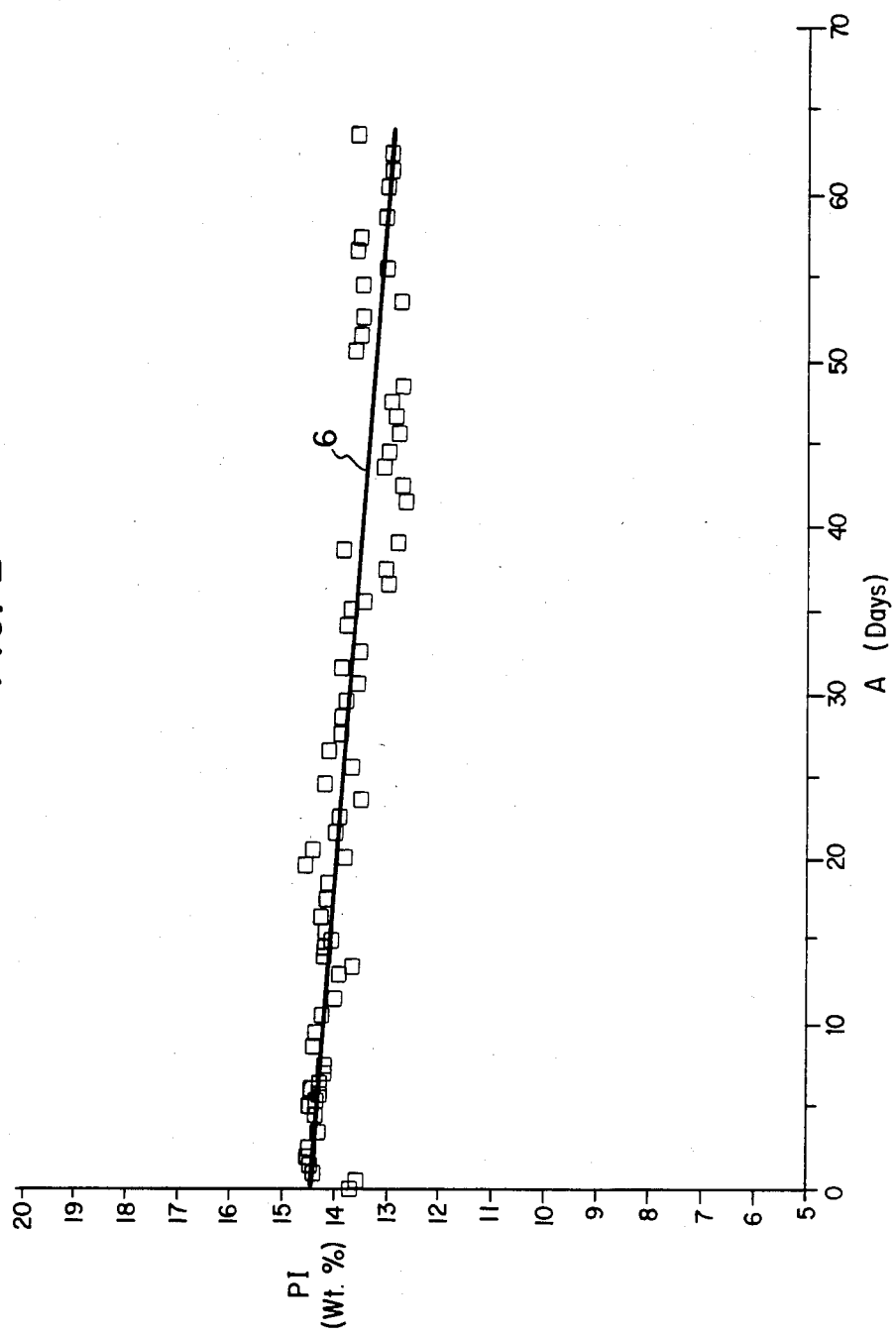

XYLENE ISOMERIZATION PROCESS

TECHNICAL FIELD

This invention relates to xylene isomerization and more particularly to xylene isomerization with co-disproportionation of ethylbenzene employing a silicalite catalyst.

ART BACKGROUND

The isomerization of xylene feedstocks is a conventional procedure in petroleum refining operations. Most such feedstocks contain the isomers ortho-, meta-, and para-xylene, and ethylbenzene together with small quantities of other aromatic compounds and saturated hydrocarbons. Xylene isomerization normally is carried out as an intermediate function in a so-called "xylene loop" in which a desired xylene isomer (usually para-xylene but in some cases also ortho-xylene) is withdrawn from a mixture of the isomers found in a process stream such as the output from a reforming unit. The remainder of the process to stream is used as a feed stock for the isomerization unit. The output from the isomerization unit is recycled and mixed with fresh charge to the xylene loop.

While ortho-xylene can be separated from the other xylene isomers and ethylbenzene by fractional distillation para-xylene which has a boiling point about 1° C. below meta-xylene and about 2° C. above ethylbenzene is normally separated in the xylene loop by crystallization or selective adsorption. Typically, the para-xylene content is reduced by the crystallization or selective adsorption step to less than 10 and preferably less than 5 weight percent. The feedstream with the para-xylene thus extracted is applied to the isomerization reactor where isomerization of the ortho- and meta-xylenes results in a product in which the para-xylene is at approximately equilibrium concentration. The procedures and reactions involved in xylene isomerization are described in greater detail in Kirk-Othmer, Encyclopedia of Chemical Technology, Third Edition, John Wiley & Sons 1984, "Xylenes and Ethylbenzene," Vol. 24, pages 709–744, to which reference is made for a more complete description of this process.

As described in the above referenced Kirk-Othmer article starting at page 732 under the heading "Zeolite-Based Xylene Isomerization," the isomerization of xylenes employing ZSM-5 type zeolite catalyst has been widely practiced. Various procedures employing such catalysts are known in the prior art. For example, U.S. Pat. No. 3,856,872 to Morrison discloses xylene isomerization using aluminosilicalite zeolite catalyst, specifically a ZSM-5 type, a ZSM-12, or a ZSM-21 catalyst. The xylene feedstream is applied, along with the hydrogen cofeed, to the isomerization reactor which is operated at a temperature of 550°–900° F. and a pressure of 150–300 psi. The Morrison isomerization step decreases the ethylbenzene and meta-xylene content of the process stream but increases the ortho-xylene along with the para-xylene content. Thus, Morrison discloses employing a nickel promoted ZSM-5 type catalyst to isomerize a feedstream containing about 17% ethylbenzene, 11% para-xylene, 65% meta-xylene and 7% ortho-xylene. The product contains about 4–6% ethylbenzene, 16–18% para-xylene, 40–43% meta-xylene or about 17–18% ortho-xylene. Somewhat similar results were achieved using nickel promoted ZSM-12 or ZSM platinum promoted ZSM-12 or nickel promoted ZSM-21 except that a somewhat less ethylbenzene reduction was observed.

U.S. Pat. No. 4,163,028 to Tabak et al discloses a xylene isomerization process employing a high silica/alumina ratio zeolite identified as ZSM-5, ZSM-11, ZSM-12, ZSM-38, ZSM-35 and ZSM-5 co-crystallized with a metal such as platinum. Typical catalysts are described as ZSM-5 having silica/alumina ratio of about 500 to 3000 or greater. The patent to Tabak et al describes the above-mentioned Morrison process as involving disproportionation of ethylbenzene and disproportionation and ethylation of xylenes. In the Tabak procedure, the isomerization reaction is carried out at a temperature above 800° F. in order to diminish the ethylbenzene concentration by dealkylation, as contrasted with the disproportionation reaction of Morrison. The Tabak et al procedure is similar to that of Morrison in that the ortho-xylene content in the product is increased, although in most cases to a somewhat lesser extent than is the case in Morrison.

U.S. Pat. No. 4,159,282 to Olsen et al discloses xylene isomerization carried out over a crystalline aluminosilicate zeolite having a crystal size of at least one micron. This catalyst can be employed alone or in combination with a crystalline aluminosilicate zeolite having a crystal size of less than one micron. The preferred crystalline aluminosilicates are said to be ZSM-5, ZSM-11, ZSM-12, ZSM-38 and ZSM-35. Olsen et al specifically discloses xylene isomerization carried out over a ZSM-5 zeolite and disclosed that a ZSM-5 zeolite having an average crystal size of about 2 microns is more xylene selective (the ratio of relative ethylbenzene loss to relative xylenes loss is greater) than a ZSM-5 catalyst having a crystal size of about 0.5 micron. The enhanced para-xylene product of the Olsen process has a reduced ethylbenzene content and a modestly decreased ortho-xylene content. Olsen et al states that the isomerization reactor may be operated to produce para-xylene as the sole product with a typical charge of 20 weight percent ethylbenzene, 51% meta-xylene, 9 weight percent para-xylene and 20 weight percent ortho-xylene, although the experimental data in the reference do not appear to support this statement.

Additional xylene isomerization processes employing aluminosilicate zeolites are disclosed in U.S. Pat. Nos. 4,188,282 and 4,218,573 to Tabak et al. The catalysts may be ZSM-5 type zeolites having silica/alumina ratios greater than 200 and preferably greater than 500. In each of these references, the conversion temperature is above 800° F. The ethylbenzene content in the isomerization feed is decreased by a mechanism which is said to involve little, if any, disproportionation. In each case, the ortho-xylene content of the product is increased substantially along with the para-xylene content.

SUMMARY OF THE INVENTION

In accordance with the present invention, there is provided a new and improved process for the isomerization of a xylene feedstock to produce a product having an enhanced para-xylene content while at the same time having a substantially reduced ethylbenzene content. In carrying out the invention, the feedstock containing a mixture of xylene isomers and ethylbenzene in which the para-xylene content is less than equilibrium and the ethylbenzene content is substantially greater than the para-xylene concentration is passed into a reaction zone containing a shape-selective crystalline silica polymorph silicalite isomerization catalyst. Hydrogen or water or both are also supplied to the reaction zone. Preferably hydrogen is supplied at a rate to provide a mole ratio of hydrogen to the composite xylene, ethylbenzene mixture within the range of 4–8. The reaction zone preferably is operated at a temperature within the range of 340°–400° C. and a hydrogen pressure within the range of 300–600 psig to effect isomerization of the xylene isomers in the feedstream to provide an increased para-xylene content and disporportionation of the ethylbenzene in the feed to provide a reduced ethylbenzene content.

BRIEF DESCRIPTION OF THE DRAWINGS

FIGS. 1 and 2 are graphs illustrating the results of experimental work relative to the present invention.

DETAILED DESCRIPTION

As indicated by the aforementioned Kirk-Othmer article at page 729, the thermodynamic equilibrium concentrations of $C_8$ aromatic isomers vary as a function of temperature. As the temperature increases, the equilibrium concentrations for ortho-xylene and ethylbenzene increase while the equilibrium concentrations for meta-xylene and para-xylene decrease, the latter at a much lower rate than the former. The reactions encountered in the isomerization of a xylene feedstream involve xylene isomerization, and transalkylation of ethylbenzene and xylenes. The xylene isomerization reaction may be characterized as involving the reaction of about three moles of meta-xylene and one mole of ortho-xylene to produce the equilibrium mixture of the three xylene isomers which is roughly two moles of meta-xylene to one mole each of ortho-and para-xylene. The ethylbenzene transalkylation reactions include disporportionation of ethylbenzene to benzene and diethylbenzene and a reaction of ethylbenzene with xylene to produce benzene and ethyldimethylbenzene. The xylene transalkylation reactions include disporportionation of xylene to toluene and trimethylbenzenes and reaction of xylene with ethylbenzene to produce toluene and ethyltoluene.

Based upon the foregoing analysis, it will be recognized that the amount of toluene in the product stream from a xylene isomerization reactor can be used as a measure of xylene loss through xylene disproportionation whereas the amount of benzene in the product stream can be used to indicate the amount of ethylbenzene disproportionation. The quantity of dimethylethylbenzene in the product in turn provides a measure of the amount of xylene lost in the ethylbenzene disporportionation.

In the present invention, xylene isomerization with co-disproportionation of ethylbenzene is carried out employing a crystalline silica polymorph silicalite catalyst. While silicalite is recognized in the art as being topologically similar to ZSM-5 zeolites, silicalite offers a significant advantage over ZSM-5 zeolites as an isomerization catalyst. The use of silicalite as the catalyst in the isomerization reaction zone provides for a substantial increase in disproportionation activity for ethylbenzene without a corresponding increase in disproportionation activity for xylene. The enhanced ethylbenzene disproportionation is indicated by a modest increase in benzene in the product with an attendant substantial decrease in ethylbenzene. This is accomplished with little or no loss in para-xylene conversion and in total xylene yield. The lack of any substantial xylene disproportionation is indicated by the low toluene content of about 1% or less in the product. Along with the substantial increase in para-xylene yield, there is no increase in ortho-xylene content as results in the use of ZSM-5 type zeolites in accordance with the procedures disclosed in the aforementioned patents to Morrison and Tabak et al. In fact, a modest decrease in ortho-xylene content is achieved.

The catalyst employed in the present invention is a crystalline silica polymorph designated in the art as "silicalite". Silicalite may be contrasted with the ZSM-5 zeolites which are characterized as aluminosilicates as disclosed in U.S. Pat. No. 3,702,886 to Argauer et al or in the case of high silica/alumina ratio (essentially aluminum-free) ZSM-5 type zeolites, as metal organosilicates as disclosed in Re 29,948 (U.S. Pat. No. 3,941,871) to Dwyer et al. Silicalite is disclosed in U.S. Pat. No. 4,061,724 to Grose et al and for further description of silicalite and its method of preparation the entire disclosure of the Grose et al patent is incorporated herein by reference. Minor amounts of aluminum, which normally will be found as an impurity in silica sources, will be present in silicalite. However, the aluminum content of silicalite is less than 1 aluminum atom for each unit cell of 96 $SiO_2$ tetrahedra.

Similarities and differences between silicalite and ZSM-5 type zeolites are examined in Debras et al "Physico-chemical characterization of pentasil type materials, I. Precursors and calcined zeolites, and II. Thermal analysis of the precursors," November 1985, Vol. 5, pp. 369–383. As explained in Debras, the ZSM-5 materials were synthesized following the teachings of the aforementioned Argauer et al patent (termed in the paper the "A" procedure) and the silicalite materials were synthesized following the teachings of the Grose et al patent (the "G" procedure).

As disclosed in Debras part I, the synthesis procedures used in the preparation of the silicalite "G" materials and the ZSM-5 zeolite "A" materials are different in several respects. The ratio of silica to the quarternary ammonium templating agent used to produce the "A" materials is much lower than the corresponding ratio used to produce the G materials. In addition, the $H_2O$/$SiO_2$ ratio for the "A" materials is substantially higher than the $H_2O$/$SiO_2$ ratio for the "G" materials.

Insofar as the materials themselves are concerned, the Debras et al paper reports several significant differences. The average crystal size of silicalite at less than 1 aluminum atom per unit cell is much greater than the average crystal size for ZSM-5 zeolite (the "A" material). Silicalite has an average crystal size greater than 5 microns. As disclosed in Debras et al. at an aluminum-/unit-cell ratio of less than 1, silicalite has an average crystal size of about 10 microns or more, whereas for ZSM-5 zeolites, the average crystal size is about 2 microns. The crystal sizes of the two materials are shown in FIGS. 3a and 3b of Part I of Debras et al. As further disclosed in Debras et al, ZSM-5 crystals have an aluminum rich core surrounded by an aluminum deficient outer shell. For the silicalite materials on the other hand, the core is aluminum deficient compared with the outer shell. That is, the aluminum gradient for silicalite is exactly opposite that of ZSM-5 zeolite. The aluminum gradients of the silicalite and ZSM-5 materials are shown in Table 3 and FIG. 5 of Debras et al, part I.

The silicalite catalyst employed in the present invention can also be used in the isomerization of xylene feedstocks in which ethylbenzene is not present in the quantities indicated previously, that is, in concentrations in excess of the para-xylene concentration. In fact, the feedstock may be substantially free of ethylbenzene. Such xylene feedstocks include substantially pure meta-xylene or mixtures of xylene isomers without ethylbenzene. In either case, the xylene feedstock is supplied to the reaction zone containing the silicalite catalysts which is operated under the conditions described previously to produce a product having an enhanced para-xylene content. The product withdrawn from the reaction zone may be subject to any suitable subsequent treatment, for example, para-xylene may be separated from the reaction zone effluent and the resulting xylene stream recycled for input into the reaction zone.

As indicated in the prior art referred to previously, it is a conventional practice to promote zeolite catalysts with various metals such as nickel and platinum. Various other metals which may be used to promote or modify zeolite catalysts include zinc, palladium, calcium, copper, magnesium, vanadium and the like. For example, the aforementioned U.S. Pat. No. 4,218,573 to Tabak et al refers to incorporating metals from groups IB through VIII of the Periodic Table into ZSM-type zeolites. Metal oxides may also be used.

The silicalite catalyst employed in the present invention can be unmodified; that is, the catalyst need not be promoted to incorporate the various metal agents which are commonly employed in the ZSM-type zeolites. In the experimental work reported herein, unmodified catalyst was used. Unmodified silicalite catalysts can be used in the isomerization of xylene feedstocks as described above in which little or no ethylbenzene is present. While unmodified silicalite catalysts are also useful where the xylene feedstock contains substantial amounts of ethylbenzene, e.g. in a concentration greater than the para-xylene concentration, in this situation, advantages may accrue in using a metal hydrogenation catalyst in combination with the silicalite. Where the feedstream contains such substantial quantities of ethylbenzene, suitable hydrogenation catalysts useful in this regard include tungsten, palladium, osmium, ruthenium, rhodium, iridium, zinc, copper, nickel, chromium, silver, zirconium, cadmium, and platinum, and oxides of such metals.

In experimental work carried out respecting the invention, silicalite catalyst was employed in the isomerization of hydrocarbon mixtures extracted from the feed stream to a commercial xylene isomerization unit. The commercial unit had a design capacity of about 31,000 barrels per day and was operated at nominal temperature and pressure conditions of about 318° C. and 250 psig.

A ZSM-5 type catalyst was employed in the commercial isomerization unit. While the exact nature of the catalyst is not available, based upon published data (Kirk-Othmer, Vol. 24, pp. 732-733), the zeolite was presumably in the NiHZSM-5 form. The xylene feedstream was supplied to the reactor to provide a space velocity (WHSV) of 7 and hydrogen cofeed was supplied to provide a ratio of hydrogen to hydrocarbons of 4.5.

A typical analysis of the xylene feedstream and the effluent product for the commercial unit are set forth below in Table I. As shown, the commercial catalyst functions to convert the xylene feedstream which is rich in ortho-and meta-isomers into an approximately equilibrium concentration of para,-meta-, and ortho-xylene. In addition, about 20% by weight of the ethylbenzene in the feedstream is disproportionated to benzene and $C_9+$ aromatic hydrocarbons.

TABLE I

|  | Feed | Effluent |
| --- | --- | --- |
| Non-Aromatics | 0 | 1.1 |
| Benzene | 0.1 | 1.9 |
| Toluene | 0.2 | 1.0 |
| Ethylbenzene | 18.6 | 15.8 |
| Paraxylene | 2.5 | 18.1 |
| Metaxylene | 53.7 | 40.9 |
| Orthoxylene | 24.6 | 16.8 |
| $C_9+$ | 0.4 | 4.4 |

The silicalite catalyst employed in the experimental work had a silica/alumina mole ratio of about 310–320 and was sodium free with a total alkali metal content calculated as potassium oxide of no more than 0.02 wt. %. The catalyst was extruded with an alumina binder into pellets having average dimensions of 1/16" diameter and 3/16" length.

The catalyst was run for a period of 14 days. At the conclusion of this period it was regenerated by passing a mixture of 90% nitrogen and 10% air over the catalyst at a temperature of about 500° C. and a pressure of 50 psig for a period of 16 hours. At the conclusion of the regeneration step, the catalyst was used further in the isomerization of a feed stream for a period of about 15 days. During the test procedure for both the fresh and regenerated catalysts the reaction temperature in the reaction vessel varied from about 250° to about 450° C. and the pressure ranged from about 200° to about 360° psig. The hydrocarbon velocity across the catalyst bed ranged from about 1 to 7 WHSV. Hydrogen was co-fed along with the xylene feed stream at rates to provide a hydrogen/hydrocarbon (the composite of the xylene and ethylbenzene content of the feed stream) molar ratio within the range of about 1 to about 12. In a few cases the isomerization reactor was run without a hydrogen cofeed.

The feedstreams employed in the experimental work included one sample formulated in the laboratory and four obtained from the actual feed to the commercial unit. Table II sets forth an average analysis in wt. % of the feedstreams employed in the experimental work and also the ranges within which the component parts vary. For example, and with reference to Table II, the ethylbenzene content in the feed ranged from a low of 17.4 wt. % to a high of 24.6 wt. % to give an average elthylbenzene content of 20.1 wt. %.

TABLE II

|  | Avg. | Range |
| --- | --- | --- |
| Non-Aromatics | 0.2 | 0–0.3 |
| Benzene | 0 | 0–0.1 |
| Toluene | 0.4 | 0.2–0.7 |
| Ethylbenzene | 20.1 | 17.4–24.6 |
| Paraxylene | 2.1 | 1.2–3.0 |
| Metaxylene | 53.8 | 51.8–56.3 |
| Orthoxylene | 22.9 | 21.2–24.8 |
| $C_9+$ | 0.5 | 0.4–0.8 |

About 45 product samples were taken and analyzed during the course of 20 runs conducted over the approximately four-week period during which the catalyst was used in either the fresh or regenerated form. Varying conditions of pressure, temperature, space velocity, and hydrogen/hydrocarbon (ethylbenzene +xylene) ratio were employed in the experimental runs as indicated by factorial design program which assumed a linear relationship between the independent variables. The results of this experimental work are reported on a sample-by-sample basis in Tables III–VI. In Tables III–VI, the experimental data reported is identified to the left of each table. The data is reported in successive columns arranged by run number and samples taken within each run. Thus, Run 1 involved three samples identified therein as samples 1.1, 1.2 and 1.3. Run 10 (Table V) involved the analysis of two samples identified as samples 10.1 and 10.2, and each of Runs 13–18 involved the analysis of only one sample. The experimental data set forth in Tables III–VI is presented in summary form in Table VII. In Table VII, the test data for each of Runs 1–18 represent an average of the results for the samples taken during the run.

Runs 1A and 1B were replicates of Run 1 carried out immediately before and after the regeneration step in order to confirm regeneration of the catalyst. These are not included in Table VII.

TABLE III

| | EXPERIMENT | | | | | | | | | | | |
|---|---|---|---|---|---|---|---|---|---|---|---|---|
| | 1 | | | 2 | | | 3 | | | 4 | | |
| | SAMPLE NUMBER | | | | | | | | | | | |
| | 1.1 | 1.2 | 1.3 | 2.1 | 2.2 | 2.3 | 3.1 | 3.2 | 3.3 | 4.1 | 4.2 | 4.3 |
| AGE OF CATALYST IN DAYS | 0.0 | 0.4 | 0.6 | 1.1 | 1.4 | 2.0 | 2.2 | 2.6 | 3.0 | 5.0 | 6.0 | 6.4 |
| AVG. BED TEMPERATURE | 371 | 370 | 369 | 251 | 251 | 251 | 442 | 441 | 442 | 347 | 350 | 350 |
| PRESSURE (PSIG) | 300 | 300 | 300 | 200 | 200 | 200 | 200 | 200 | 200 | 360 | 360 | 360 |
| LIQUID ANALYSIS WT. % | | | | | | | | | | | | |
| NON-AROM | 0.3 | 0.4 | 0.4 | 0.4 | 0.6 | 0.7 | 0.6 | 0.6 | 0.8 | 0.7 | 0.7 | 0.4 |
| BZ | 3.4 | 3.0 | 2.7 | 0.7 | 0.3 | 0.2 | 4.2 | 6.1 | 6.9 | 2.8 | 2.9 | 3.3 |
| TOL | 0.9 | 0.7 | 0.7 | 0.4 | 0.4 | 0.4 | 1.9 | 2.4 | 5.4 | 0.8 | 0.7 | 0.8 |
| EB | 11.7 | 12.7 | 13.2 | 18.4 | 18.2 | 17.3 | 8.1 | 8.3 | 4.9 | 10.9 | 11.1 | 11.1 |
| P-XYL | 16.6 | 16.4 | 16.4 | 5.7 | 5.6 | 6.0 | 17.5 | 17.2 | 16.9 | 17.9 | 17.8 | 17.8 |
| O-XYL | 18.5 | 18.6 | 19.0 | 23.1 | 22.5 | 22.8 | 19.7 | 18.6 | 18.0 | 18.3 | 18.2 | 18.0 |
| M-XYL | 42.7 | 43.6 | 43.3 | 51.4 | 51.7 | 51.6 | 42.4 | 41.4 | 40.4 | 43.0 | 42.9 | 42.0 |
| TOTAL XYL | 77.8 | 78.6 | 78.7 | 80.2 | 79.8 | 80.4 | 79.6 | 77.2 | 75.3 | 79.2 | 78.9 | 77.8 |
| C9+ | 5.9 | 4.6 | 4.3 | 0.3 | 0.8 | 1.0 | 5.6 | 5.4 | 6.7 | 5.6 | 5.7 | 6.6 |
| M-ET | 2.3 | 2.5 | 2.7 | 2.8 | 1.8 | 1.8 | | | | | | |
| P-ET | 1.2 | 1.3 | 1.5 | 1.5 | 0.9 | 1.0 | | | | | | |
| O-ET | 0.6 | 0.7 | 0.7 | 0.1 | 0.5 | 0.5 | | | | | | |
| 1,3,5-TMB | 3.5 | 3.8 | 3.7 | 3.4 | 4.0 | 4.1 | | | | | | |
| 1,2,4-TMB | 9.1 | 10.0 | 9.7 | 8.8 | 10.5 | 10.5 | | | | | | |
| 1,2,3-TMB | 1.4 | 1.5 | 1.5 | 1.3 | 1.6 | 1.6 | | | | | | |
| TOTAL HEAVIES | 24.0 | 24.4 | 24.1 | 18.2 | 20.1 | 20.5 | 5.6 | 5.4 | 6.7 | 5.6 | 5.7 | 6.6 |
| EB RATE (MOLES/MIN) | 0.00290 | 0.00290 | 0.00290 | 0.00041 | 0.00041 | 0.00041 | 0.00290 | 0.00290 | 0.00290 | 0.00041 | 0.00041 | 0.00041 |
| XYL RATE (MOLES/MIN) | 0.01104 | 0.01104 | 0.01104 | 0.00158 | 0.00158 | 0.00158 | 0.01104 | 0.01104 | 0.01104 | 0.00158 | 0.00158 | 0.00158 |
| H2 RATE (MOLES/MIN) | 0.06473 | 0.06473 | 0.06473 | 0.00000 | 0.00000 | 0.00000 | 0.06473 | 0.06473 | 0.06473 | 0.02321 | 0.02286 | 0.02286 |
| H2/HC MOLAR RATIO | 4.589 | 4.589 | 4.589 | 0.000 | 0.000 | 0.000 | 4.589 | 4.589 | 4.589 | 11.519 | 11.342 | 11.342 |
| LHSV | 7.00 | 7.00 | 7.00 | 1.00 | 1.00 | 1.00 | 7.00 | 7.00 | 7.00 | 1.00 | 1.00 | 1.00 |
| MHSV | 6.83 | 6.83 | 6.83 | 0.98 | 0.98 | 0.98 | 6.83 | 6.83 | 6.83 | 0.98 | 0.98 | 0.98 |
| XYLENE CONVERSION | | | | | | | | | | | | |
| M-XYLENE CONV. | 11.9 | 16.7 | 16.8 | 17.5 | 9.4 | 9.5 | 9.6 | 10.9 | 11.5 | 12.4 | 9.8 | 9.9 | 11.0 |
| O-XYLENE CONV. | 7.2 | 8.4 | 8.6 | 8.5 | 4.5 | 5.2 | 4.9 | 4.5 | 5.5 | 6.0 | 5.7 | 5.8 | 6.1 |
| P-XYLENE PRODUC | 16.6 | 12.5 | 12.0 | 11.9 | 3.3 | 3.2 | 3.5 | 15.8 | 15.6 | 15.4 | 16.4 | 16.3 | 16.2 |
| XYLENE CONSUMPTION | | | | | | | | | | | | |
| % XYLENES RECOV | 96.8 | 84.0 | 82.9 | 81.9 | 86.6 | 85.4 | 85.9 | 100.4 | 98.3 | 96.2 | 101.1 | 100.8 | 99.0 |
| TOLUENE YIELD | 0.6 | 0.4 | 0.2 | 0.2 | −0.1 | −0.1 | −0.1 | 1.5 | 2.0 | 5.0 | 0.4 | 0.3 | 0.4 |
| ETHYLBENZENE DISPROPORT. | | | | | | | | | | | | |
| % EB CONSUMED | 23.1 | 52.0 | 49.1 | 47.8 | 24.5 | 26.0 | 29.7 | 61.2 | 59.8 | 76.2 | 47.1 | 46.1 | 46.3 |
| BENZENE YIELD | 2.0 | 2.9 | 2.5 | 2.9 | 0.6 | 0.3 | 0.2 | 4.5 | 6.4 | 6.9 | 2.8 | 2.9 | 3.3 |
| HEAVIES YIELD | 4.0 | 19.9 | 19.8 | 19.3 | 15.0 | 16.5 | 16.8 | 5.2 | 5.0 | 6.3 | 5.2 | 5.3 | 6.2 |

TABLE IV

| | EXPERIMENT | | | | | | | | | | |
|---|---|---|---|---|---|---|---|---|---|---|---|
| | 1 | | | 6 | 7 | | | 8 | | | 1 |
| | SAMPLE NUMBER | | | | | | | | | | |
| | 5.1 | 5.2 | 5.3 | 6.1 | 7.1 | 7.2 | 7.3 | 8.1 | 8.2 | 8.3 | 1.1 | 1.2 |
| AGE OF CATALYST IN DAYS | 7.0 | 8.0 | 8.5 | 8.8 | 8.9 | 9.0 | 9.2 | 9.4 | 9.6 | 10.0 | 13.0 | 14.0 |
| AVG. BED TEMPERATURE | 253 | 251 | 251 | 252 | 438 | 440 | 440 | 250 | 250 | 250 | 375 | 375 |
| PRESSURE (PSIG) | 360 | 360 | 360 | 360 | 360 | 360 | 360 | 250 | 250 | 250 | 300 | 300 |
| LIQUID ANALYSIS WT. % | | | | | | | | | | | | |

TABLE IV-continued

| | EXPERIMENT | | | | | | | | | | | |
|---|---|---|---|---|---|---|---|---|---|---|---|---|
| | 1 | | | 6 | 7 | | | 8 | | | 1 | |
| | SAMPLE NUMBER | | | | | | | | | | | |
| | 5.1 | 5.2 | 5.3 | 6.1 | 7.1 | 7.2 | 7.3 | 8.1 | 8.2 | 8.3 | 1.1 | 1.2 |
| NON-AROM | 0.7 | 0.7 | 0.7 | 0.6 | 0.7 | 1.0 | 0.9 | 0.8 | 0.4 | 0.4 | 0.3 | 0.3 |
| BZ | 0.0 | 0.0 | 0.0 | 0.0 | 0.6 | 4.7 | 5.1 | 0.1 | 0.1 | 0.1 | 2.4 | 2.5 |
| TOL | 0.4 | 0.4 | 0.4 | 0.4 | 0.8 | 16.2 | 15.6 | 0.4 | 0.5 | 0.4 | 0.7 | 0.6 |
| EB | 18.7 | 18.7 | 18.6 | 18.6 | 17.6 | 2.9 | 3.0 | 18.5 | 21.2 | 21.7 | 12.8 | 13.8 |
| P-XYL | 4.2 | 4.1 | 4.1 | 5.2 | 7.5 | 13.6 | 14.1 | 4.5 | 2.2 | 1.2 | 11.2 | 10.8 |
| O-XYL | 23.0 | 23.1 | 23.2 | 22.9 | 22.0 | 15.1 | 15.6 | 22.9 | 22.7 | 22.8 | 20.8 | 20.9 |
| M-XYL | 52.9 | 53.0 | 52.9 | 52.9 | 50.4 | 33.7 | 34.6 | 52.6 | 52.6 | 52.4 | 48.0 | 47.7 |
| TOTAL XYL | 80.1 | 80.2 | 80.2 | 81.0 | 79.9 | 62.4 | 64.3 | 80.0 | 77.5 | 76.4 | 80.0 | 79.4 |
| C9+ | 0.1 | 0.0 | 0.0 | 0.1 | 0.4 | 12.8 | 11.6 | 0.2 | 0.2 | 1.0 | 3.8 | 3.4 |
| M-ET | | 1.9 | 2.4 | 2.5 | 2.3 | 0.4 | | | | | | |
| P-ET | | 1.0 | 1.3 | 1.3 | 1.3 | 0.2 | | | | | | |
| O-ET | | 0.5 | 0.6 | 0.7 | 0.6 | 0.1 | | | | | | |
| 1,3,5,-TMB | | 2.1 | 2.4 | 2.4 | 2.2 | 0.3 | | | | | | |
| 1,2,4-TMB | | 5.4 | 6.3 | 6.3 | 5.7 | 1.0 | | | | | | |
| 1,2,3-TMB | | 0.8 | 0.9 | 0.9 | 0.8 | 0.1 | | | | | | |
| TOTAL HEAVIES | 0.1 | 11.7 | 13.9 | 14.2 | 13.3 | 14.9 | 11.6 | 0.2 | 0.2 | 1.0 | 3.8 | 3.4 |
| EB RATE (MOLES/MIN) | 0.00290 | 0.00290 | 0.00290 | 0.00041 | 0.00041 | 0.00041 | 0.00041 | 0.00041 | 0.00041 | 0.00041 | 0.00290 | 0.00290 |
| XYL RATE (MOLES/MIN) | 0.01104 | 0.01104 | 0.01104 | 0.00158 | 0.00158 | 0.00158 | 0.00158 | 0.00158 | 0.00158 | 0.00158 | 0.01104 | 0.01104 |
| H2 RATE (MOLES/MIN) | 0.06473 | 0.06473 | 0.06473 | 0.00000 | 0.00000 | 0.00000 | 0.00000 | 0.01438 | 0.02549 | 0.02406 | 0.07009 | 0.07009 |
| H2/HC MOLAR RATIO | 4.589 | 4.589 | 4.589 | 0.000 | 0.000 | 0.000 | 0.000 | 7.133 | 12.649 | 11.940 | 4.968 | 4.968 |
| LHSV | 7.00 | 7.00 | 7.00 | 1.00 | 1.00 | 1.00 | 1.00 | 1.00 | 1.00 | 1.00 | 7.00 | 7.00 |
| WHSV | 6.83 | 6.83 | 6.83 | 0.98 | 0.98 | 0.98 | 0.98 | 0.98 | 0.98 | 0.98 | 6.83 | 6.83 |
| XYLENE CONVERSION | | | | | | | | | | | | |
| M-XYLENE CONV. | 11.9 | −0.1 | 5.4 | 6.3 | 6.7 | 8.2 | 19.8 | 18.4 | 0.2 | 0.1 | 0.4 | 4.9 | 5.1 |
| O-XYLENE CONV. | 7.2 | 1.0 | 3.3 | 3.6 | 4.1 | 4.5 | 9.2 | 8.5 | 1.1 | 1.3 | 1.2 | 3.2 | 3.1 |
| P-XYLENE PRODUC | 16.6 | 2.7 | 2.2 | 2.1 | 3.0 | 5.1 | 11.8 | 12.5 | 3.0 | 0.7 | −0.3 | 9.7 | 9.3 |
| XYLENE CONSUMPTION | | | | | | | | | | | | |
| % XYLENES RECOV | 96.8 | 102.3 | 91.6 | 90.0 | 90.1 | 90.4 | 78.1 | 81.7 | 102.2 | 99.1 | 97.6 | 101.9 | 101.3 |
| TOLUENE YIELD | 0.6 | 0.0 | 0.0 | 0.0 | −0.1 | 0.3 | 15.5 | 15.1 | 0.0 | 0.1 | 0.0 | 0.3 | 0.2 |
| ETHYLBENZENE DISPROPORT. | | | | | | | | | | | | |
| % EB CONSUMED | 32.1 | 9.2 | 18.8 | 20.7 | 21.3 | 24.3 | 86.2 | 85.5 | 10.2 | −3.0 | −5.3 | 38.0 | 33.1 |
| BENZENE YIELD | 2.0 | 0.0 | 0.0 | 0.0 | 0.0 | 0.5 | 4.6 | 5.1 | 0.1 | 0.1 | 0.1 | 2.4 | 2.5 |
| HEAVIES YIELD | 4.0 | −0.3 | 10.1 | 11.8 | 12.0 | 11.4 | 14.2 | 11.2 | −0.2 | −0.2 | 0.6 | 3.4 | 3.0 |

TABLE V

| | EXPERIMENT | | | | | | | | | | | |
|---|---|---|---|---|---|---|---|---|---|---|---|---|
| | 1 | | | | | 9 | | | 10 | | 11 | |
| | SAMPLE NUMBER | | | | | | | | | | | |
| | 1.1 | 1.2 | 1.3 | 1.4 | 1.5 | 9.1 | 9.2 | 9.3 | 10.1 | 10.2 | 11.1 | 11.2 |
| AGE OF CATALYST IN DAYS | 1.0 | 2.0 | 3.0 | 4.0 | 5.0 | 5.3 | 5.5 | 6.0 | 6.4 | 7.0 | 8.0 | 8.4 |
| AVG. BED TEMPERATURE | 371 | 374 | 370 | 371 | 370 | 350 | 348 | 352 | 248 | 252 | 453 | 453 |
| PRESSURE (PSIG) | 300 | 300 | 300 | 300 | 300 | 305 | 300 | 300 | 300 | 300 | 200 | 200 |
| LIQUID ANALYSIS WT. % | | | | | | | | | | | | |
| NON-AROM | 0.3 | 0.2 | 0.2 | 0.2 | 0.3 | 0.2 | 0.3 | 0.4 | 0.2 | 0.4 | 0.5 | 0.5 |
| BZ | 2.0 | 2.0 | 1.9 | 1.7 | 1.9 | 2.7 | 2.3 | 3.1 | 0.1 | 0.0 | 6.8 | 6.7 |
| TOL | 0.7 | 0.7 | 0.7 | 0.7 | 0.9 | 0.8 | 0.8 | 0.9 | 0.6 | 0.6 | 5.4 | 5.5 |
| EB | 13.8 | 13.4 | 13.7 | 13.6 | 13.8 | 11.2 | 12.8 | 10.8 | 17.8 | 20.1 | 5.3 | 5.2 |
| P-XYL | 14.6 | 14.4 | 14.4 | 143 | 14.6 | 17.8 | 15.5 | 17.8 | 3.8 | 1.3 | 16.8 | 16.9 |
| O-XYL | 19.8 | 19.8 | 19.8 | 19.9 | 19.8 | 18.2 | 19.2 | 18.2 | 22.4 | 22.2 | 18.1 | 18.0 |
| M-XYL | 45.6 | 46.3 | 46.1 | 46.4 | 46.2 | 42.8 | 42.5 | 43.4 | 54.8 | 55.1 | 40.4 | 40.5 |
| TOTAL XYL | 80.0 | 80.5 | 80.3 | 80.6 | 80.6 | 78.8 | 77.2 | 79.4 | 81.0 | 78.6 | 75.3 | 75.4 |
| C9+ | 3.2 | 3.2 | 3.2 | 3.2 | 3.2 | 6.2 | 6.3 | 5.4 | 0.3 | 0.3 | 6.7 | 6.6 |
| M-ET | | | | | | | | | | | | |
| P-ET | | | | | | | | | | | | |
| O-ET | | | | | | | | | | | | |
| 1,3,5-TMB | | | | | | | | | | | | |
| 1,2,4-TMB | | | | | | | | | | | | |
| 1,2,3-TMB | | | | | | | | | | | | |
| TOTAL HEAVIES | 3.2 | 3.2 | 3.2 | 3.2 | 3.2 | 6.2 | 6.3 | 5.4 | 0.3 | 0.3 | 6.7 | 6.6 |
| EB RATE (MOLES/MIN) | 0.00290 | 0.00290 | 0.00290 | 0.00290 | 0.00290 | 0.00041 | 0.00041 | 0.00041 | 0.00207 | 0.00207 | 0.00124 | 0.00124 |
| XYL RATE (MOLES/MIN) | 0.01104 | 0.01104 | 0.01104 | 0.01104 | 0.01104 | 0.00158 | 0.00158 | 0.00158 | 0.00788 | 0.00788 | 0.00473 | 0.00473 |

TABLE V-continued

| | EXPERIMENT | | | | | | | | | | | |
|---|---|---|---|---|---|---|---|---|---|---|---|---|
| | 1 | | | | | 9 | | | 10 | | 11 | |
| | SAMPLE NUMBER | | | | | | | | | | | |
| | 1.1 | 1.2 | 1.3 | 1.4 | 1.5 | 9.1 | 9.2 | 9.3 | 10.1 | 10.2 | 11.1 | 11.2 |
| H2 RATE (MOLES/MIN) | 0.06473 | 0.06473 | 0.06473 | 0.06473 | 0.06473 | 0.01339 | 0.01339 | 0.01339 | 0.05580 | 0.05580 | 0.00893 | 0.00893 |
| H2/HC MOLAR RATIO | | 4.589 | 4.589 | 4.589 | 4.589 | 4.589 | 6.646 | 6.646 | 6.646 | 5.538 | 5.538 | 1.477 | 1.477 |
| LHSV | | 7.00 | 7.00 | 7.00 | 7.00 | 7.00 | 1.00 | 1.00 | 1.00 | 5.00 | 5.00 | 3.00 | 3.00 |
| WHSV | | 6.83 | 6.83 | 6.83 | 6.83 | 6.83 | 0.98 | 0.98 | 0.98 | 4.88 | 4.88 | 2.93 | 2.93 |
| XYLENE CONVERSION | | | | | | | | | | | | | |
| M-XYLENE CONV. | 11.9 | 7.2 | 6.7 | 6.7 | 6.6 | 7.1 | 10.0 | 10.2 | 9.6 | −1.8 | −2.3 | 12.4 | 12.3 |
| O-XYLENE CONV. | 7.2 | 4.2 | 4.3 | 4.2 | 4.2 | 4.4 | 5.8 | 4.7 | 5.9 | 1.7 | 1.8 | 5.9 | 6.0 |
| P-XYLENE PRODUC | 16.6 | 13.1 | 12.9 | 12.9 | 12.7 | 12.9 | 16.3 | 14.0 | 16.2 | 2.3 | −0.2 | 15.3 | 15.4 |
| XYLENE CONSUMPTION | | | | | | | | | | | | | |
| % XYLENES RECOV | 96.8 | 102.2 | 102.5 | 102.6 | 102.5 | 101.9 | 100.7 | 98.9 | 100.9 | 103.0 | 100.4 | 96.2 | 96.3 |
| TOLUENE YIELD | 0.6 | 0.3 | 0.3 | 0.3 | 0.3 | 0.5 | 0.4 | 0.4 | 0.5 | 0.2 | 0.2 | 5.0 | 5.1 |
| ETHYLBENZENE DISPROPORT. | | | | | | | | | | | | | |
| % EB CONSUMED | 23.1 | 33.0 | 35.2 | 33.5 | 34.2 | 33.7 | 45.6 | 37.7 | 47.8 | 13.9 | 2.4 | 74.3 | 74.8 |
| BENZENE YIELD | 2.0 | 2.0 | 2.3 | 1.9 | 2.0 | 2.2 | 2.7 | 2.3 | 3.6 | 0.5 | 0.0 | 6.8 | 6.8 |
| HEAVIES YIELD | 4.0 | 2.8 | 2.8 | 2.8 | 2.8 | 2.8 | 5.8 | 5.9 | 5.0 | −0.1 | −0.1 | 6.3 | 6.2 |

TABLE VI

| | EXPERIMENT | | | | | | | | |
|---|---|---|---|---|---|---|---|---|---|
| | 12 | | | 13 | 14 | 15 | 16 | 17 | 18 |
| | SAMPLE NUMBER | | | | | | | | |
| | 12.1 | 12.2 | 12.3 | 13.1 | 14.1 | 15.1 | 16.1 | 17.1 | 18.1 |
| AGE OF CATALYST IN DAYS | 10.0 | 11.0 | 13.0 | 13.2 | 13.4 | 13.2 | 15.0 | 15.3 | 15.4 |
| AVG. BED TEMPERATURE | 357 | 356 | 352 | 351 | 362 | 384 | 383 | 393 | 401 |
| PRESSURE (PSIG) | 360 | 360 | 360 | 360 | 360 | 360 | 360 | 360 | 360 |
| LIQUID ANALYSIS WT. % | | | | | | | | | |
| NON-AROM | 0.3 | 0.3 | 0.3 | 0.3 | 0.3 | 0.2 | 0.2 | 0.3 | 0.3 |
| BZ | 2.3 | 2.3 | 2.6 | 1.8 | 2.3 | 2.4 | 2.3 | 2.4 | 2.4 |
| TOL | 0.8 | 0.8 | 0.8 | 0.7 | 0.8 | 0.8 | 0.8 | 0.8 | 0.8 |
| EB | 11.7 | 11.7 | 11.7 | 13.2 | 12.3 | 11.7 | 12.3 | 12.1 | 12.1 |
| P-XYL | 16.8 | 16.8 | 16.9 | 15.2 | 15.9 | 15.3 | 14.7 | 13.7 | 14.0 |
| O-XYL | 18.9 | 18.9 | 18.9 | 19.6 | 19.4 | 19.7 | 19.8 | 20.2 | 20.3 |
| M-XYL | 44.9 | 44.9 | 44.5 | 45.9 | 45.0 | 45.6 | 46.1 | 46.8 | 46.2 |
| TOTAL XYL | 80.6 | 80.6 | 80.3 | 80.7 | 80.3 | 80.6 | 80.6 | 80.7 | 80.5 |
| C9+ | 4.3 | 4.3 | 4.3 | 3.3 | 4.0 | 4.3 | 3.8 | 3.7 | 3.9 |
| M-ET | | | | | | | | | |
| P-ET | | | | | | | | | |
| O-ET | | | | | | | | | |
| 1,3,5-TMB | | | | | | | | | |
| 1,2,4-TMB | | | | | | | | | |
| 1,2,3-TMB | | | | | | | | | |
| TOTAL HEAVIES | 4.3 | 4.3 | 4.3 | 3.3 | 4.0 | 4.3 | 3.8 | 3.7 | 3.9 |
| EB RATE (MOLES/MIN) | 0.00041 | 0.00041 | 0.00041 | 0.00124 | 0.00124 | 0.00207 | 0.00249 | 0.00249 | 0.00249 |
| XYL RATE (MOLES/MIN) | 0.00158 | 0.00158 | 0.00158 | 0.00473 | 0.00473 | 0.00788 | 0.00946 | 0.00946 | 0.00946 |
| H2 RATE (MOLES/MIN) | 0.01116 | 0.01071 | 0.01027 | 0.02232 | 0.02232 | 0.03750 | 0.06473 | 0.06473 | 0.06473 |
| H2/HC MOLAR RATIO | 5.538 | 5.317 | 5.095 | 3.692 | 3.692 | 3.722 | 5.353 | 5.353 | 5.353 |
| LHSV | 1.00 | 1.00 | 1.00 | 3.00 | 3.00 | 5.00 | 6.00 | 6.00 | 6.00 |
| WHSV | 0.98 | 0.98 | 0.98 | 2.93 | 2.93 | 4.88 | 5.86 | .5.86 | 5.86 |
| XYLENE CONVERSION | | | | | | | | | |
| M-XYLENE CONV. | 11.9 | 8.1 | 8.1 | 8.3 | 6.9 | 7.8 | 7.2 | 6.7 | 6.0 | 6.6 |
| O-XYLENE CONV. | 7.2 | 5.2 | 5.2 | 5.1 | 4.4 | 4.6 | 4.3 | 4.2 | 3.8 | 3.7 |
| P-XYLENE PRODUC | 16.6 | 15.2 | 15.2 | 15.4 | 13.7 | 14.4 | 13.8 | 13.2 | 12.2 | 12.5 |
| XYLENE CONSUMPTION | | | | | | | | | |
| % XYLENES RECOV | 96.8 | 102.5 | 102.5 | 102.6 | 103.1 | 102.6 | 102.9 | 102.9 | 103.1 | 102.8 |
| TOLUENE YIELD | 0.6 | 0.4 | 0.4 | 0.4 | 0.3 | 0.4 | 0.4 | 0.4 | 0.4 | 0.4 |
| ETHYLBENZENE DISPROPORT. | | | | | | | | | |
| % EB CONSUMED | 23.1 | 43.4 | 43.4 | 43.2 | 35.9 | 40.3 | 43.2 | 40.3 | 41.3 | 41.3 |
| BENZENE YIELD | 2.0 | 2.7 | 2.7 | 2.6 | 1.8 | 2.3 | 2.4 | 2.3 | 2.4 | 2.4 |
| HEAVIES YIELD | 4.0 | 3.9 | 3.9 | 3.9 | 2.9 | 3.6 | 3.9 | 3.4 | 3.3 | 3.5 |

TABLE VII

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| TEMP. | 370 | 251 | 442 | 349 | 251 | 252 | 439 | 250 | 350 | 250 | 453 | 355 | 351 | 362 | 384 | 383 | 393 | 401 |
| PRESS. | 300 | 200 | 200 | 360 | 360 | 360 | 360 | 250 | 302 | 300 | 200 | 360 | 360 | 360 | 360 | 360 | 360 | 360 |
| LSHV | 7.0 | 1.0 | 7.0 | 1.0 | 7.0 | 1.0 | 1.0 | 1.0 | 1.0 | 5.0 | 3.0 | 1.0 | 3.0 | 3.0 | 5.0 | 6.0 | 6.0 | 6.0 |

TABLE VII-continued

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| WHSV | 6.8 | 1.0 | 6.8 | 1.0 | 6.8 | 1.0 | 1.0 | 1.0 | 1.0 | 4.9 | 2.9 | 1.0 | 2.9 | 2.9 | 4.9 | 5.9 | 5.9 | 5.9 |
| H2/HC | 4.59 | 0.00 | 4.59 | 11.40 | 4.59 | 0.00 | 0.00 | 10.57 | 6.65 | 5.54 | 1.48 | 5.32 | 3.69 | 3.69 | 3.72 | 5.35 | 5.35 | 5.35 |
| NON-AROM | 0.3 | 0.5 | 0.7 | 0.6 | 0.6 | 0.5 | 0.8 | 0.5 | 0.3 | 0.3 | 0.5 | 0.3 | 0.3 | 0.3 | 0.2 | 0.2 | 0.3 | 0.3 |
| BENZENE | 2.5 | 0.3 | 5.7 | 3.0 | 0.0 | 0.0 | 3.4 | 0.1 | 2.7 | 0.0 | 6.7 | 2.4 | 1.8 | 2.3 | 2.4 | 2.3 | 2.4 | 2.4 |
| TOLUENE | 0.6 | 0.3 | 3.2 | 0.8 | 0.4 | 0.3 | 10.7 | 0.4 | 0.8 | 0.6 | 5.4 | 0.8 | 0.7 | 0.8 | 0.8 | 0.8 | 0.8 | 0.8 |
| EB | 10.4 | 15.1 | 7.1 | 11.0 | 17.3 | 16.2 | 7.1 | 20.5 | 11.6 | 18.9 | 5.2 | 11.7 | 13.2 | 12.3 | 11.7 | 12.3 | 12.1 | 12.1 |
| P-XYLENE | 13.6 | 4.8 | 17.1 | 17.8 | 3.8 | 4.5 | 11.3 | 2.6 | 17.0 | 2.5 | 16.8 | 16.8 | 15.2 | 15.9 | 15.3 | 14.7 | 13.7 | 14.0 |
| O-XYLENE | 15.5 | 19.2 | 18.7 | 18.1 | 21.3 | 19.9 | 16.6 | 22.8 | 18.5 | 22.3 | 18.0 | 18.8 | 19.6 | 19.4 | 19.7 | 19.8 | 20.2 | 20.3 |
| M-XYLENE | 35.8 | 43.3 | 41.2 | 42.6 | 48.9 | 46.1 | 37.4 | 52.6 | 42.9 | 54.8 | 40.4 | 44.6 | 45.9 | 45.0 | 45.6 | 46.1 | 46.8 | 46.2 |
| TOTAL XYL | 64.9 | 67.3 | 77.0 | 78.5 | 74.1 | 70.6 | 65.3 | 78.0 | 78.4 | 79.6 | 75.3 | 80.3 | 80.7 | 80.3 | 80.6 | 80.6 | 80.7 | 80.5 |
| HEAVIES | 20.0 | 16.5 | 5.9 | 6.0 | 7.6 | 12.4 | 12.6 | 0.5 | 6.0 | 0.3 | 6.6 | 4.3 | 3.3 | 4.0 | 4.3 | 3.8 | 3.7 | 3.9 |
| M-XYL CON | 17.0 | 9.5 | 11.6 | 10.2 | 3.9 | 6.7 | 15.4 | 0.2 | 9.9 | −2.0 | 12.4 | 8.2 | 6.9 | 7.8 | 7.2 | 6.7 | 6.0 | 6.6 |
| O-XYL CON | 8.5 | 4.8 | 5.3 | 5.9 | 2.7 | 4.1 | 7.4 | 1.2 | 5.5 | 1.7 | 6.0 | 5.2 | 4.4 | 4.6 | 4.3 | 4.2 | 3.8 | 3.7 |
| P-XYL PRO | 12.1 | 3.3 | 15.6 | 16.3 | 2.3 | 3.0 | 9.8 | 1.1 | 15.5 | 1.0 | 15.3 | 15.3 | 13.7 | 14.4 | 13.8 | 13.2 | 12.2 | 12.5 |
| % XYL REC | 82.9 | 86.0 | 98.3 | 100.3 | 94.6 | 90.1 | 83.4 | 99.6 | 100.2 | 101.7 | 96.2 | 102.5 | 103.1 | 102.6 | 102.9 | 102.9 | 103.1 | 102.8 |
| TOL YIELD | 0.2 | −0.1 | 2.8 | 0.4 | 0.0 | −0.1 | 10.3 | 0.0 | 0.4 | 0.2 | 5.0 | 0.4 | 0.3 | 0.4 | 0.4 | 0.4 | 0.4 | 0.4 |
| % EB CONS | 49.6 | 26.7 | 65.7 | 46.5 | 16.2 | 21.3 | 65.3 | 0.6 | 43.7 | 8.2 | 74.5 | 43.4 | 35.9 | 40.3 | 43.2 | 40.3 | 41.3 | 41.3 |
| BZ YIELD | 2.5 | 0.3 | 6.4 | 3.0 | 0.0 | 0.0 | 3.7 | 0.4 | 2.7 | 0.0 | 6.7 | 2.4 | 1.8 | 2.3 | 2.4 | 2.3 | 2.4 | 2.4 |
| C9+ | 19.7 | 16.1 | 5.5 | 5.6 | 7.2 | 12.0 | 12.3 | 0.1 | 5.6 | −0.1 | 6.3 | 3.9 | 2.9 | 3.6 | 3.9 | 3.4 | 3.3 | 3.5 |

The xylene isomerization process of the present invention is temperature and pressure dependent as shown by the experimental work reported in Tables II–VI. In the summary of results set forth in Table VII, Runs 2, 5, 6, 8 and 10 produced poor results in terms of para-xylene yield and ethylbenzene disproportionation. In these runs, the temperature was about 250° C. and the pressure varied from 200–360 psig. Clearly superior results, as indicated by isomerization of xylenes to the para-isomer and by ethylbenzene consumption, are shown in Runs 3, 4, 9, 11 and 12. Here the temperature ranged from about 350°–450° C. and the pressure from about 200–360 psig. A hydrogen pressure of 200 psig was adequate to produce good results at higher temperatures of about 440°–450° C., whereas at lower temperatures of about 350° C., a pressure in excess of about 300 psig was consistent with good para-xylene production and ethylbenzene disproportionation.

Normally the reaction zone temperature will be within the range of 340° C.–450° C. Preferably, the isomerization reaction zone is operated at a hydrogen pressure (or hydrogen partial pressure where the hydrogen stream is not 100% pure hydrogen) in excess of 300 psig in order to allow the isomerization reaction to proceed at moderate temperatures of about 400° C. or less while disproportionating a substantial amount of ethylbenzene in the feed stream. The preferred reaction temperature is within the range of about 340°–380° C. and the preferred hydrogen pressure is within the range of about 325–500 psig and preferably 350–400 psig. Pressures below 300 psig should normally be avoided since as indicated by the above-experimental data, relatively low pressures require high reaction temperatures. Pressures above about 500 psig usually would impose expensive design considerations in the plant without a corresponding benefit, and it usually will be desirable to operate at a pressure of less than 500 psig.

It will be recognized that temperature and pressure gradients and variations, usually small, will exist across the catalyst bed and the temperatures and pressures given herein are average values. For example, in a typical catalyst bed there may be a decrease in pressure across the bed of from 5–10 psi. Similarly, the temperature across the bed may vary by a small amount, usually no more than 5°–15° C. with the outlet temperature usually being a few degrees higher than the inlet temperature. In addition, the average temperature of the bed normally will be increased modestly as the catalyst ages and the temperatures set forth herein are those existing in the reaction zone when the catalyst is fresh. For example, where the reaction zone is initially operated at a temperature of 350° C., this may be progressively increased in one or more increments throughout the life of the catalyst (before regeneration) to arrive at a final temperature of about 50°–100° C. higher than the initial temperature. After regeneration of the catalyst, the reaction temperature may then be reduced to its initial value and again progressively increased until the next regeneration step.

The hydrogen co-feed, while not necessary for the isomerization reaction, is highly desirable in order to prevent coking of the silicalite catalyst which results in a premature loss of activity. As indicated by the experimental data, the molar ratio of hydrogen to hydrocarbons (the composite of xylenes and ethylbenzenes in the feed) may vary from about 1 to about 11. Hydrogen/hydrocarbon molar ratios within this range produced good results in terms of para-xylene yield and ethylbenzene disproportionation. Preferably, the hydrogen/hydrocarbon molar ratio is within the range of 4–8. As indicated by further experimental data discussed below, a particularly preferred range for the hydrogen/hydrocarbon molar ratio is 5.5–7.5. The space velocity of the feedstream over the catalyst bed may likewise vary over a wide range. For reasons of economy, it usually will be desirable to provide a WHSV of at least one. Typically, the space velocity may vary between about 1–10 WHSV and preferably is within the range of 3–8.

Additional experimental work was carried out over a prolonged period of time in order to determine the effect of catalyst age on the xylene isomerization and ethylbenzene disproportionation reactions. In this procedure, which was carried out over a period of more than two months, the bulk of the experiment was conducted at an average temperature of about 380° C. and an average pressure of about 360 psig. After running the test for about six weeks, the temperature was increased by an increment of 5° C., and after an additional 10 days, the temperature was again increased by an increment of 5° C. Two feedstreams were employed in this test procedure. Feed #1 was employed throughout most of the test. Shortly after the first incremental temperature increase, feed #2 was started and employed for the remainder of the test. The compositions of these two feeds are set forth below in Table VIII.

TABLE VIII

|  | Feed 1 | Feed 2 |
| --- | --- | --- |
| Non-Aromatics | 0.23 | 0.2 |
| Benzene | 0.04 | 0.03 |
| Toluene | 0.65 | 0.5 |
| Ethylbenzene | 17.4 | 24.6 |
| Paraxylene | 3.0 | 1.2 |
| Orthoxylene | 21.9 | 21.2 |
| Metaxylene | 56.3 | 51.8 |
| $C_9+$ | 0.46 | 0.47 |

The results of this experimental work are set forth in FIG. 1 which is a graph showing the weight percent, P, in the effluent of ethylbenzene and para-xylene plotted on the ordinate versus the age of the catalyst, A, in days plotted on the abscissa. In FIG. 1, the ethylbenzene content is indicated by curve 2 and the para-xylene content by curve 4. The time of the first incremental temperature increase is indicated by $T_1$, the second incremental increase by $T_2$, and the point at which the second feed was commenced by $F_2$.

In view of the lower para-xylene content of feed #2, as compared with feed #1, and since the para-xylene itself does not enter into the xylene isomerization reaction, values indicative of the incremental increase in para-xylene content were arrived at by subtracting the para-xylene content in the feed from the para-xylene content in the effluent. The results of this treatment of data are set forth in FIG. 2, in which curve 6 is a graph of the incremental increase in para-xylene content, PI in wt. %, plotted on the ordinate versus the catalyst age in days plotted on the abscissa.

As shown in FIGS. 1 and 2, there is a relatively steady rate of catalyst deactivation with time as indicated by the increased ethylbenzene content and the decreased para-xylene content in the effluent from the reactor bed. The experimental data reported in FIGS. 1 and 2 indicate that the deactivation rate for the silicalite catalyst is greater than that of the ZSM-5 type catalyst employed in the commercial unit. However, consistent with the data presented earlier, the silicalite catalyst exhibits a substantially better activity for ethylbenzene disproportionation than does the ZSM-5 type catalyst. It will also be recognized that the increase in temperature had a fairly significant impact upon the xylene disproportionation reaction. In fact, before the temperature increase, curve 2 indicative of ethylbenzene content showed a tendency to stabilize around 11%.

Throughout the course of the experimental work depicted in FIGS. 1 and 2, the hydrogen/hydrocarbon molar ratio was kept at a relatively constant value of about 4.3-4.5 and the space velocity was maintained at a value of about 7.1 WHSV. The para-xylene content in the effluent continued to show a progressive decline. The hydrogen feed rate was increased to provide a hydrogen/hydrocarbon molar ratio of about 6.5. This resulted in an initial decline in para-xylene content from about 13.3 to 12.9 wt. %. The initial decline in para-xylene content is thought to result from the decrease in conversion normally associated with an increase in gas rate. However, the para-xylene content thereafter remained relatively constant (within +or −0.2 wt. %) for a period of five days, providing a modest increase in the slope of the para-xylene decay line. Thus, the increase of the hydrogen/hydrocarbon molar ratio resulted in an improvement in the aging quality of the catalyst.

As disclosed in U.S. Pat. Nos. 4,387,260 to Watson et al and 4,587,371 to Forward et al, water may be employed in conversion reactions involving the alkylation of aromatic compounds over a silicalite catalyst. The water functions to prolong the life of the catalyst. For example, as disclosed in the aforementioned patent to Watson et al, steam co-feed in an amount within the range of about 20,000–60,000 ppm based upon the aromatic feed, functions to extend the activity of the catalyst for the alkylation of benzene with ethylene and to improve the selectivity of the catalyst for the desired ethylbenzene product.

The efficacy of the water in prolonging the effective life of catalyst is believed to reside in its function to prevent coking of the catalyst. In the present invention, water (normally in the form of steam) can be employed in conjunction with the hydrogen co-feed, or in some cases, as a substitute for the hydrogen, in order to retard catalyst coking. The steam co-feed may be supplied in an amount within the range of 0.1–10 wt. % of the hydrocarbon feed (the composite of ethylbenzene and xylenes) and preferably in an amount within the range of about 1–6 wt. %. Where steam co-feed is employed, the hydrogen feed rate may be reduced, and in some cases, even eliminated, although it usually will be preferred to maintain the hydrogen feed.

Having described specific embodiments of the present invention, it will be understood that modification thereof may be suggested to those skilled in the art, and it is intended to cover all such modifications as fall within the scope of the appended claims.

We claim:

1. In a process for the isomerization of a xylene feed stock to produce a product having an enhanced para-xylene content and a diminished ethylbenzene content, the steps comprising:
   a. passing said xylene feed stock containing a mixture of xylene isomers and ethylbenzene in which para-xylene is present in less than an equilibrium amount and ethylbenzene is present in a concentration greater than the para-xylene concentration into a reaction zone and in contact with a shape-selective crystalline silica polymorph silicalite isomerization catalyst,
   b. supplying hydrogen or water or mixture thereof to said reaction zone,
   c. operating said reaction zone at temperature and pressure conditions to effect isomerization of xylene isomers to provide an increased para-xylene content and disproportionation of ethylbenzene to provide a reduced ethylbenzene content, and
   d. withdrawing a product of increased para-xylene content and a diminished ethylbenzene content from said reaction zone, the para-xylene content in said product being greater than the ethylbenzene content thereof.

2. The method of claim 1 wherein water is supplied to said reaction zone in an amount within the range of 0.1–10 wt. % of the amount of ethylbenzene and xylene in said feedstock.

3. The method of claim 2 wherein said water is provided to said reaction zone in an amount within the range of 1–6 wt. % of ethylbenzene and xylene in said feedstock.

4. The method of claim 1 wherein hydrogen and water are supplied to said reaction zone.

5. The method of claim 1 wherein said feed stream contains ortho-xylene in an amount greater than the para-xylene content of said feed stream and wherein the isomerization product withdrawn from said reaction zone contains a lower ortho-xylene content than said feed stream.

6. In a process for the isomerization of a xylene feed stock to produce a product having an enhanced para-xylene content and a diminished ethylbenzene content, the steps comprising:
  a. passing said xylene feede stock containing a mixture of xylene isomers in which the ortho-xylene content is greater than the para-xylene content and ethylbenzene in which para-xylene is present in less than an equilibrium amount and ethylbenzene is present in a concentration greater than the para-xylene concentration into a reaction zone and in contact with a shape-selective crystalline silica polymorph silicalite isomerization catalyst,
  b. supplying hydrogen to said reaction zone at a hydrogen pressure of at least 200 psig,
  c. operating said reaction zone at temperature and pressure conditions to effect isomerization of xylene isomers to provide an increased para-xylene content and a lower ortho-xylene content than said feed stock and disproportionation of ethylbenzene to provide a reduced ethylbenzene content, and
  d. withdrawing a product of increased para-xylene content and a diminished ortho-xylene content and ethylbenzene content from said reaction zone.

7. The method of claim 6 wherein the para-xylene content of the product withdrawn from the reaction zone is greater than the ethylbenzene content thereof.

8. The method of claim 6 wherein said reaction zone is operated at a temperature with the range of 340–450° C.

9. The method of claim 6 wherein said reaction zone is operated at a hydrogen pressure greater than 300 psig.

10. The method of claim 9 wherein said reaction zone is operated at a temperature no greater than 400° C.

11. The method of claim 6 wherein said reaction zone is operated at a hydrogen pressure of at least 350 psig and at a temperature within the range of 340–380° C.

12. The method of claim 6 wherein hydrogen is supplied to said reaction zone at a rate to provide a mole ratio of hydrogen to the composite of xylene and ethylbenzene in said feed stream within the range of 1–11.

13. The method of claim 12 wherein said hydrogen is supplied to said reaction at a rate to provide a mole ratio of hydrogen to the composite of xylene and ethylbenzene in said feedstream within the ratio of 4–8.

14. The method of claim 13 wherein said hydrogen is supplied to said reaction zone at a rate to provide a hydrogen/xylene and ethylbenzene mole ratio the range of 5.5–7.5.

15. The method of claim 6 wherein said xylene feedstock is supplied to said reaction zone to provide a space velocity over said catalyst within the range of 1–10 WHSV.

16. The method of claim 15 wherein said space velocity is within the range of 3–8 WHSV.

* * * * *